United States Patent [19]

Detty et al.

[11] Patent Number: 5,766,236
[45] Date of Patent: Jun. 16, 1998

[54] ELECTRICAL STIMULATION SUPPORT BRACES

[76] Inventors: Gerald D. Detty, 3911 W. Lambert La., Tucson, Ariz. 85742; Thomas J. McEnany, 2006 Salt Myrtle La.; Ira S. Rothholz, 2270 Kensington La., both of Orange Park, Fla. 32073

[21] Appl. No.: 635,308

[22] Filed: Apr. 19, 1996

[51] Int. Cl.$^6$ ..................................... A61N 1/04
[52] U.S. Cl. .................. 607/149; 607/108; 607/112; 607/152; 607/115; 602/2
[58] Field of Search .................. 607/149, 152–153, 607/108, 112, 114; 219/522–529; 128/639–640, 643; 602/2

[56] References Cited

U.S. PATENT DOCUMENTS

| | | |
|---|---|---|
| 4,708,149 | 11/1987 | Axelgaard et al. |
| 4,722,354 | 2/1988 | Axelgaard et al. |
| 5,336,255 | 8/1994 | Kanare et al. |
| 5,397,338 | 3/1995 | Grey et al. .................. 607/149 X |
| 5,601,618 | 2/1997 | James .................. 607/149 X |

Primary Examiner—Jennifer Bahr
Assistant Examiner—Ryan Carter
Attorney, Agent, or Firm—Caesar, Rivise, Bernstein, Cohen & Pokotilow, Ltd.

[57] ABSTRACT

A brace for disposition on a part of a person to provide heat retention, electrical stimulation, compression and/or support thereto. The brace basically comprises a sleeve for disposition around the body part, an electrically conductive fabric located on the inner surface of the sleeve, and at least one electrical connector, e.g. a snap means, for releasable electrical connection to an electric source providing High Voltage Pulsed Current. The sleeve is formed of an electrically insulative, thermally insulative, resilient or elastomeric material, e.g., neoprene rubber. The electrically conductive fabric is stretchable and flexible and arranged for direct engagement with the skin of the person when the brace is in place so that electrical stimulation is provided to the body part by the engagement of the electrically conductive fabric to the skin, while the sleeve retains heat in the portion of the person's body about which the sleeve is disposed and also provides mechanical compression and/or support.

8 Claims, 3 Drawing Sheets

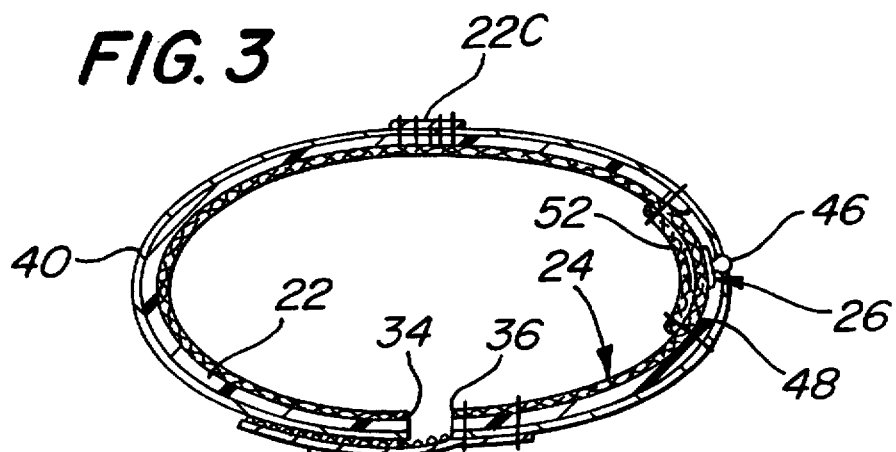
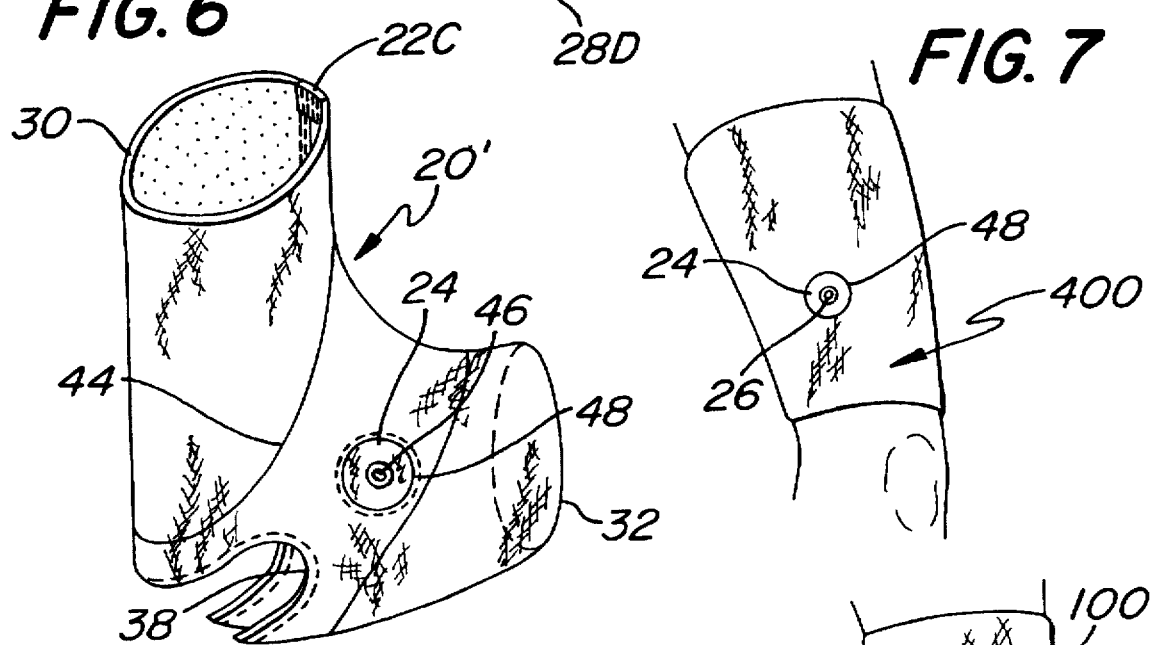
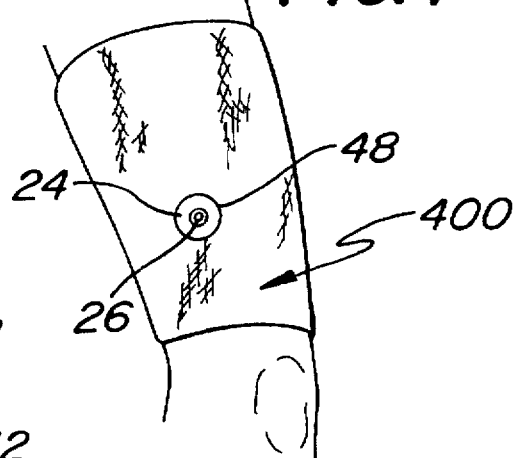
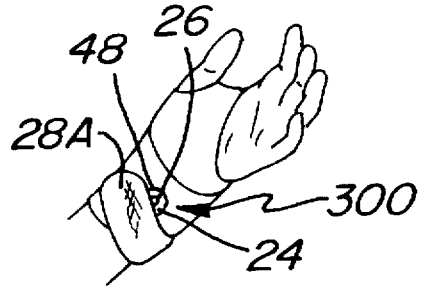
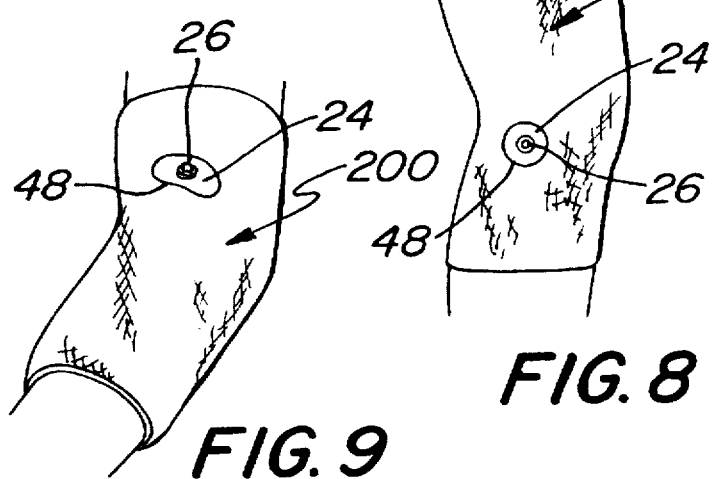

ELECTRICAL STIMULATION SUPPORT BRACES

BACKGROUND OF THE INVENTION

This invention relates generally to braces to provide support for limb and in particular to braces which include electrical stimulation means.

Persons engaged in athletic activities involving walking, running and/or jumping, frequently utilize some support means on their limbs to protect a joint from a sprain or other injury, or to facilitate the healing of an already injured ankle while protecting it from exacerbation.

U. S. Pat. No. 5,336,255 (Kanare) discloses an electrical stimulation heat/cool pack to be applied to a portion, e.g., the back, of a person. The pack includes a nonconductive pouch and straps for positioning and holding the pouch against the portion of the person's body to be treated. Flexible conductive fabric patches are provided, either permanently attached or removably attached, to the pouch along with electrical lead wires for connecting the patches to a remote pulse generator. An electrically conductive adhesive gel pad is also provided to releasably couple the flexible conductive fabric patch to the portion of the person's body to be treated.

U. S. Pat. Nos. 4,708,149 (Axelgaard et al.) and 4,722,354 (Axelgaard et al.) each disclose a transcutaneous nerve and/or muscle stimulation electrode which is arranged to be contoured to the skin areas of a patient.

Electrical stimulation to body parts has also been accomplished by use of an electrically conductive fabric, such as that sold by Prizm Medical, Inc. of Norcross Georgia. That fabric has been made into items, e.g., gloves, sleeves, and socks, for disposition on the body part to be treated.

While the aforementioned prior art approaches for providing electrical stimulation to body parts may be generally suitable for their intended purposes, they still leave much to be desired from various standpoints. Examples of such drawbacks are, suitability for treatment of chronic problems, suitability for use on a wide variety of portions of the user's body (e.g., knee, ankle, wrist, elbow, etc.), ease of application, connection and use, effectiveness in providing therapeutic action (e.g., combining electrical stimulation, with heat retention and mechanical support and/or compression), simplicity of construction, cost, ruggedness, and ability to be used during athletic competition, events, or other strenuous activities.

Thus, a need presently exists for a brace which addresses those needs of the prior art.

OBJECTS OF THE INVENTION

Accordingly, it is the general object of the instant invention to provide a brace which addresses the needs of the prior art.

It is a further object of the instant invention to provide a brace which provides mechanical support, heat retention and electrical stimulation to a portion of a person's body on which the brace is located.

It is a further object of the instant invention to provide a brace which is easy to apply and use on a portion of a limb of a person and which provides mechanical support, heat retention and electrical stimulation to that portion of a person's body.

It is a further object of the instant invention to provide a brace which provides mechanical support, heat retention and electrical stimulation and which is simple in construction, and easy and inexpensive to manufacture.

SUMMARY OF THE INVENTION

These and other objects of the instant invention are achieved by providing a brace for disposition on a limb of a person to provide mechanical support, heat retention, and electrical stimulation thereto. The brace basically comprises sleeve means, electrically conductive terminal means, and releasable electrical connector means.

The sleeve means is formed of an electrically insulative, thermally insulative, resilient or elastomeric material, e.g., neoprene rubber, and is arranged to be disposed around and releasably secured to the portion of the person's body to treated. The sleeve means has an inner surface, portions of which engage the skin of the person when the sleeve means is in place.

The conductive terminal means comprises a stretchable, flexible, electrically conductive fabric which is secured to a portion of the inner surface of the sleeve means for direct engagement with the skin of the person.

The electrical connector means comprises an electrically conductive member, e.g., a snap, fixedly secured to the conductive fabric and in electrical continuity therewith. The electrical conductive member is arranged to be releasably secured to a source of electrical energy so that electrical stimulation is provided by the engagement of the electrically conductive fabric to the skin of the patient, while the sleeve retains heat in the portion of the person's body about which the sleeve is disposed and also provides mechanical compression and/or support.

Each brace of this invention is arranged to be readily releasably mounted on the portion of the person's body to be treated.

Depending upon the construction desired the sleeve means may comprise a preformed tubular sleeve arranged to be slid over the body party to be treated, or a sheet arranged to be wrapped around the body part to form a sleeve and once wrapped to be secured via releasable, e.g., hook and loop fastening means. Brace constructions making use of releasably securable fastening means to enable the sheet to be wrapped around the portion of the body to be treated and to be held in place thereon have the advantage of enabling the brace to accommodate various size persons. Hence such constructions can be considered "universal" or "one-size-fits-all" designs.

DESCRIPTION OF THE DRAWING

Other objects and many of the intended advantages of this invention will be readily appreciated when the same becomes better understood by reference to the following detailed description, when considered in connection with the accompanying drawing wherein:

FIG. 3 is an enlarged sectional view take along line 3—3 of FIG. 2;

FIG. 6 a view similar to FIG. 2 but showing an alternative embodiment of an ankle brace constructed in accordance with this invention;

FIG. 7 is an illustration of a thigh brace constructed in accordance with this invention and shown mounted in place on the thigh of a person;

FIG. 8 is an illustration of a knee brace constructed in accordance with this invention and shown mounted in place on the knee of a person;

FIG. 9 is an illustration of an elbow brace constructed in accordance with this invention and shown mounted in place on the elbow of a person; and FIG. 10 is an illustration of a wrist brace constructed in accordance with this invention and shown mounted in place on the wrist of a person.

DETAILED DESCRIPTION OF THE PREFERRED EMBODIMENTS

Figure 1:
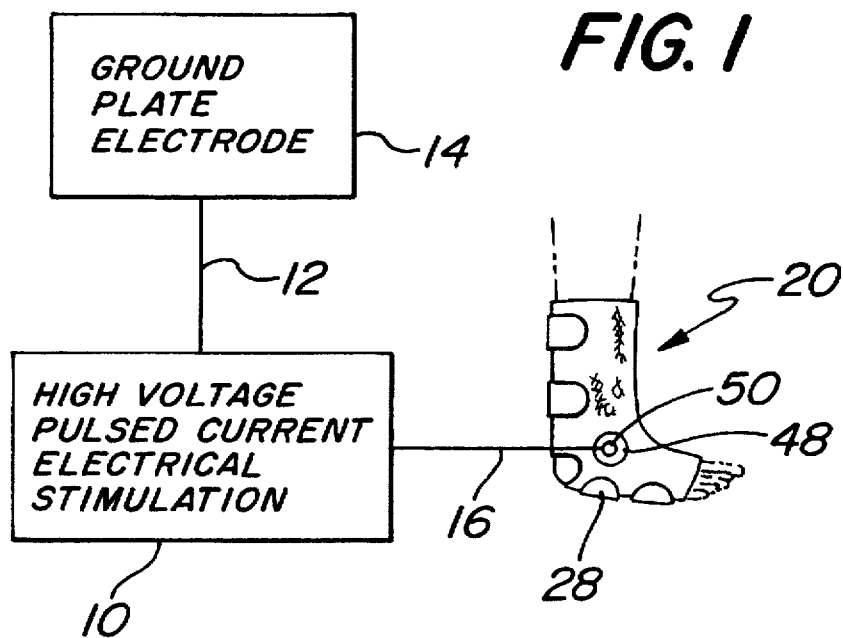
FIG. 1 is a schematic illustration of an ankle brace constructed in accordance with this invention shown mounted on the ankle of a person and connected to an electrical stimulation unit and to a body contacting electrode.

Referring now in greater detail to the various figures of the drawing, wherein like reference characters refer to like parts, there is shown in FIGS. 1–5 one embodiment of an ankle brace 20 constructed in accordance with the teachings of the present invention. The brace 20 is of the "wrap-around type", i.e., is in the form of a sheet which is arranged to be wrapped about the ankle to form a sleeve. Securement means, in the form of mounting straps (to be described later) are provided to hold the sleeve in place on the ankle, as shown in FIG. 1. In FIG. 6 there is shown an alternative embodiment of an ankle brace 20' constructed in accordance with this invention. The brace 20', unlike brace 20, is preformed into a sleeve for application onto the ankle (again like shown in FIG. 1).

It must be pointed out at this juncture that braces constructed in accordance with this invention can be of the "wraparound type" or the "preformed type." In addition, such braces be constructed for use on other joints, such as the knee, elbow, wrist. To that end, braces for such applications are shown in FIGS. 8, 9, and 10, respectively, and are designated by the reference numerals 100, 200, and 300, respectively. In fact, braces of this invention can be configured to be used on any limb portion or other portion of a person's body which would benefit from the application of electrical stimulation, heat retention, compression and/or support thereto. One such application is shown in FIG. 7, where a thigh brace 400 is shown.

Figure 2:
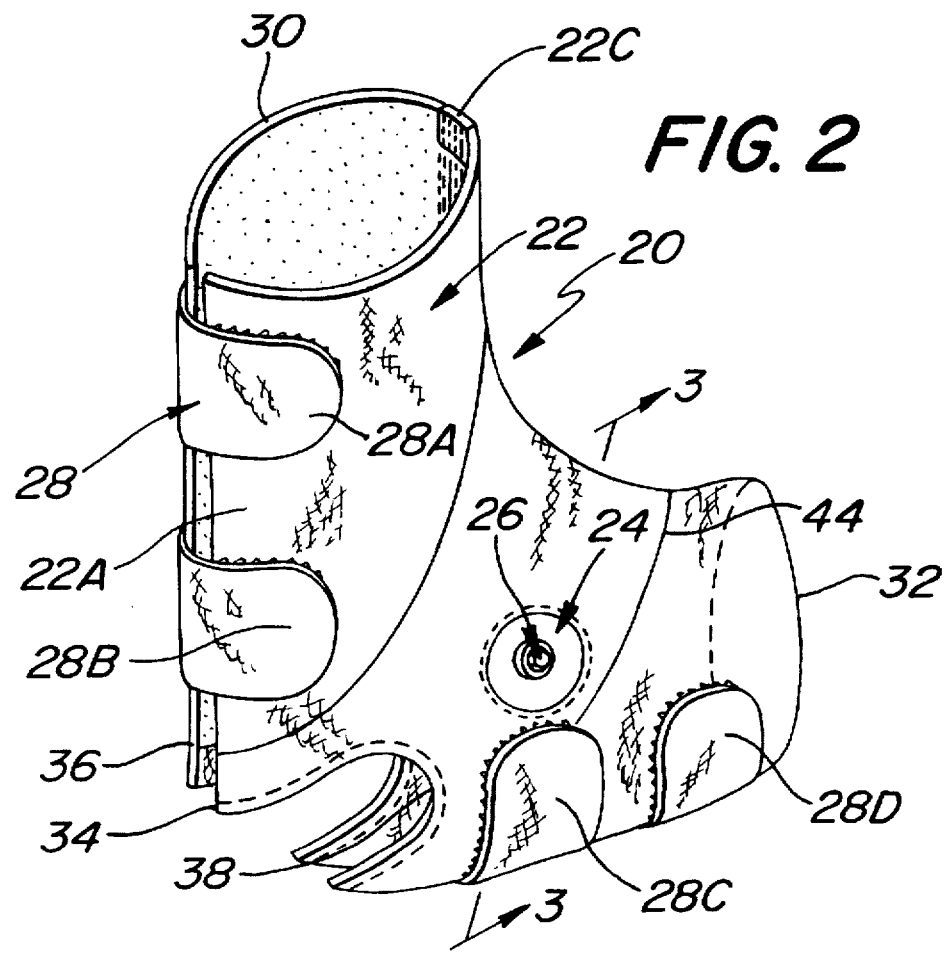
FIG. 2 is an enlarged isometric view of one embodiment of an ankle brace constructed in accordance with this invention.

As can be seen clearly in FIG. 2 the brace 20 basically comprises a sheet-like member 22 arranged to be bent or wrapped into a sleeve, an electrically conductive terminal 24, at least one electrically conductive connector 26, and mounting straps 28. Since the member 22 is arranged to be wrapped into a tubular or sleeve-like configuration for application to the body part to be treated, the member 22 will be referred to hereinafter as a sleeve member. The sleeve member 22 is formed of a sheet of an elastomeric material which is cut into a predetermined shape, depending upon the type of the brace to be produced, e.g., ankle, knee, elbow, wrist, thigh, etc. In the embodiment shown herein the sleeve member 22 is made up of two similarly shaped sheets 22A and 22B (FIGS. 4 and 5) which are secured together, e.g., sewn, along a common, fabric-reinforced, seam line 22C to form an integral sheet. The sheet can, if desired, be formed as a one piece or unitary construction in lieu of the two sheets. In any case the sleeve member 22 includes a top edge 30, a bottom edge 32 and a pair of marginal side edges 34 and 36. Each of the side edges includes a recess 38 therein.

The sleeve member is arranged to be placed on the wearer's ankle and wrapped or bent thereabout into a tubular configuration so that the marginal side edges 34 and 36 are disposed immediately adjacent each other along the posterior side of the leg contiguous with the ankle and along the under side of the foot contiguous with the ankle as shown in FIG. 1. When so mounted the top edge 30 of the brace 20 is disposed adjacent the wearer's calf, and the bottom edge is adjacent the wearer's toes, and the two recesses 38 conjoin to form an opening through which the wearer's heel extends.

The elastomeric material making up the sleeve member for a wrap-around brace is preferably a fabric-coated neoprene, with the fabric 40 (FIG. 4) being fixedly secured, e.g., glued, to the entire outer surface of the neoprene sheet. The fabric 40 is tufted or plush so that it can act as the multiple loop fastening component of a hook and loop, e.g., Velcro®, fastening system to cooperate with multiple hook components forming the straps 28 and thereby facilitate the mounting of the brace on the portion of the wearer's body.

The mounting straps 28 comprise an upper pair 28A and 28B, and a lower pair 28C. Each of the straps is a strip or web of a multi-hook component of the VELCRO® hook and loop fastening system. Each of the straps is fixedly secured to, e.g., sewn, to sleeve member adjacent the marginal side edge 36, so that they each project from respective portions of that edge, and with the multiple hooks thereof facing the interior surface of the sleeve member 22. Thus, when the sleeve member is fit about the ankle of the wearer, the upper pair of mounting straps 28A and 28B can be brought over the adjacent portions of the sleeve contiguous with the opposite marginal edge 34 to releasably engage the multiple loops forming the plush fabric of the sleeve. In a similar manner, the lower pair of mounting straps 28C and 28D can be brought over the adjacent portions of the sleeve contiguous with the opposite marginal edge 34 to releasably engage the multiple loops forming the plush fabric of the sleeve. The amount of overlap of each of the straps 28A–28D is independently adjustable to accommodate a wide variation in the size of ankle on which the brace 20 can be used.

Figure 5:
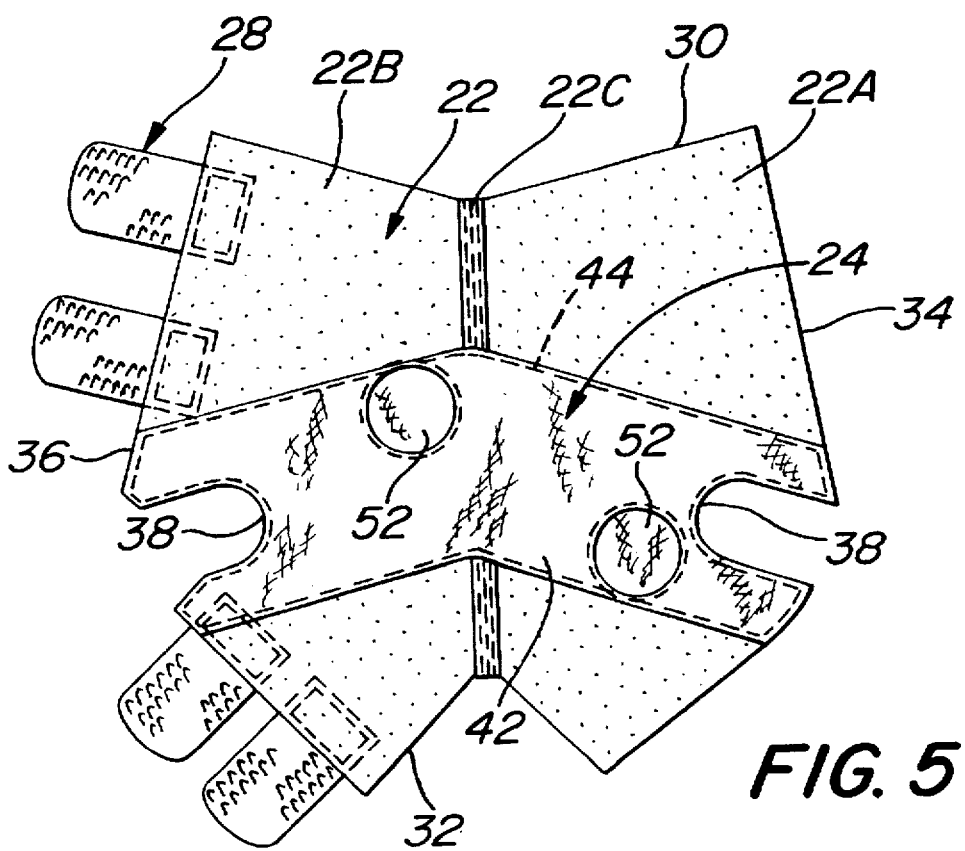
FIG. 5 is an enlarged plan view of the interior surface of the ankle brace of FIG. 2 when laid flat, i.e., prior to application on the ankle of a person.

Referring now to FIG. 5 the construction of the electrical terminal means 24 will now be described. Such means is provided to serve as one electrode of any conventional electrical stimulation, e.g., a High Voltage Pulsed Current (HVPC), system. That system is shown in FIG. 1 and basically comprises an HVPC unit 10 having a pair of output terminals. One of the output terminals is electrically connected via a conductor wire 12 to a ground plate electrode 14. The ground plate electrode is an electrically conductive, flexible, sheet-like member of a substantial area and which is arranged to be placed in contact with any desired portion of the body of the person, e.g., in contact with the skin in the small of the back. The other output terminal of the HVPC unit 10 is arranged to be electrically releasably connected, via a wire 16 to the electrode 24 of the ankle brace 20. That electrode is in the form of a sheet or web 42 of electrically conductive flexible, stretchable fabric or mesh. One particularly suitable fabric is that sold by neumed, Inc. of Lawrenceville, NJ under the trademark Theraknit. That fabric basically comprises a plurality of silver coated nylon fibers. The weaving of these fibers into a fabric results in a fabric having very good electrical conductivity, with very low inherent resistance. Thus, the fabric is an even electrical conductor (i.e., it doesn't produce localized heated areas or "hot spots" due to uneven conductivity). Moreover, the material making up the fibers does not produce much lint, which could result in the creation of hot spots due to the increased electrical resistance of small lint particles.

The silver coated nylon fibers are flexible so that the resulting fabric is soft, flexible, and somewhat stretchable.

As can be seen clearly in FIG. 5 the electrically conductive fabric web 42 encompasses a large area and extends across the interior surface of the sleeve member from portions thereof on each side of the recess 38 to the seam 22C. The fabric 42 is secured along its periphery to the sleeve member by lines of stitching 44.

Electrical continuity to the fabric 42 is provided by the heretofore identified quick operating electrical connectors 26. Each of those connectors comprises an electrically conductive male snap member fixedly secured to the fabric. The projecting end 46 of each snap extends through a respective hole 48 in the sleeve member to be available for connection by a pair of mating female snap 50 (FIG. 1). The female snaps are electrically connected to the end of the conductor wire 16 from the electrical stimulation unit 10. Thus, when the female snaps 50 are releasably secured to the male snaps 26, electrical continuity is provided between the output terminal of the electrical stimulation unit 10 and the ankle skin contacting electrode 24, via the conductor 16 and the mating male and female snaps. It must be pointed out at this juncture that electrical continuity to the conductive fabric 42 may be achieved by means of only a single male connector 26 or by any number of such connectors and located at any desired position with respect to the fabric 42. Moreover, the female snap members may be fixedly secured to the fabric 24 of the brace, while the male connectors are fixedly secured to the end of the conductor wire 16 from the electrical stimulation unit. Further still, other types of releasably securable electrical connectors may be used in the brace.

As can be seen in FIG. 5 pair of circular patches 50 of the same type of material as that forming the sleeve are secured, e.g., sewn, over the fabric portion of the fabric web 42 on the inner surface thereof at the location of the holes 48. The patches 50 serve as a back-up for the electrically conductive snaps 26 located threat and isolate those snaps from the skin of the wearer in the interest of comfort.

Figure 4:
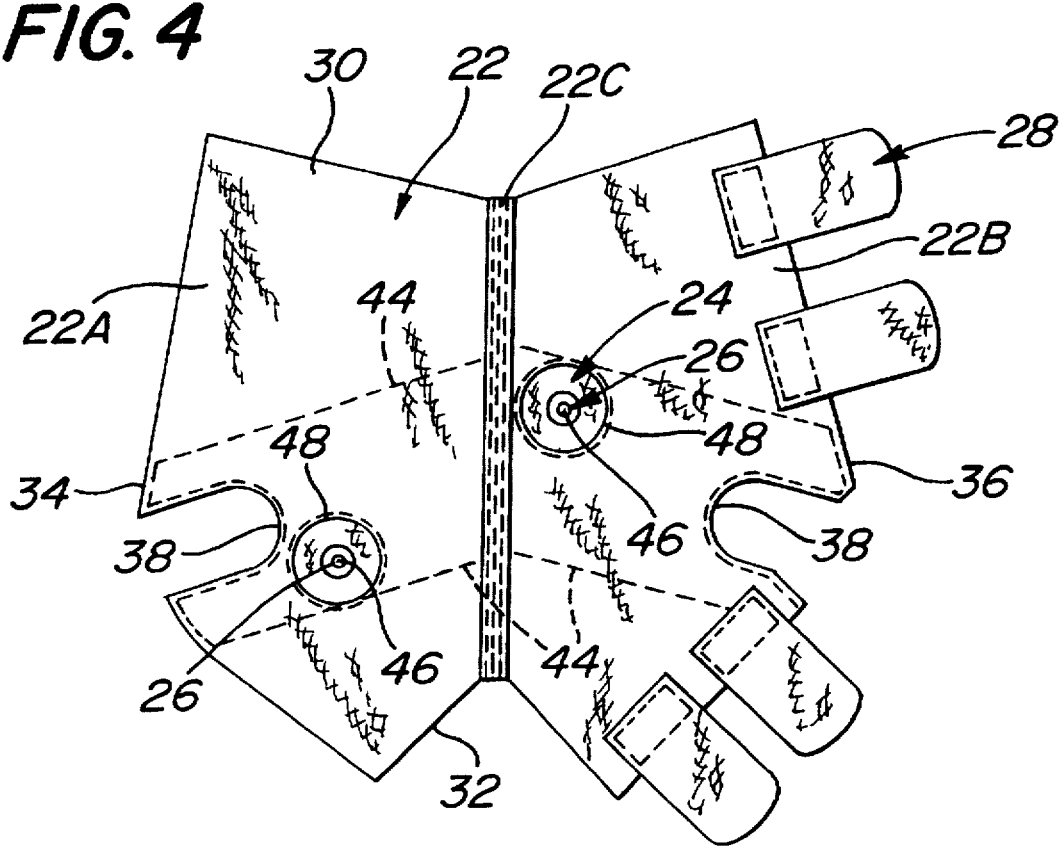
FIG. 4 is an enlarged plan view of the exterior surface of the ankle brace of FIG. 2 when laid flat, i.e., prior to application on the ankle of a person.

It must be pointed out at this juncture that the electrically conductive fabric web 42 can be of any shape desired, and can cover as much of the inner surface of the brace as desired. Thus, the fabric 42 can be made to cover the entire inner surface of the brace or only a portion (as shown in FIGS. 2, 4, and 5).

The preformed-sleeve brace 20' of FIG. 6 is of similar construction to the brace 20 except that the sleeve member is formed from a unitary or single sheet of fabric covered neoprene. In this regard the preformed sheet of neoprene is seamed along the seam line 22C to form the preformed sleeve shown in FIG. 6. Inasmuch as the sleeve 22 is a preformed sleeve there is no need for mounting straps 28A–28D or plush fabric covering to on the sleeve (although a fabric covering for the neoprene may be desired for other than securement reasons). In all other respects the brace 20' is identical to the brace 20.

Like the ankle braces 20 and 20' described heretofore, the thigh brace 400 of FIG. 7, the knee brace 100 of FIG. 8, the elbow brace 200 of FIG. 9, and the wrist brace 300 of FIG. 10, may be either preformed sleeve constructions or wrap-around sleeve constructions. Moreover, they may include one or more electrical contacts 26 extending through opening in the sleeve and in communication with the electrically conductive fabric on the inner surface of the sleeve for releasable securement to a mating snap(s) forming a portion of the electrical stimulation system.

In accordance with commercial embodiments of this invention the neoprene making up the braces of this invention is preferably of a substantial thickness, e.g. approximately 3 mm. thick, to provide cushioning, heat retention, compression and support. The substantial thickness of the preferred neoprene material of the brace, coupled with its thermally insulative properties, insures that when a brace constructed in accordance with this invention is worn, heat will be retained under the brace, thereby keeping the wrapped body part at an elevated temperature. This elevated temperature at the affected body part can facilitate healing of an injury or prevent the exacerbation thereof, particularly when combined with electrical stimulation threat. The elevated temperature results in a slight amount of skin perspiration under the brace. This perspiration serves to increase the conductivity of the mesh to the skin, thereby enhancing the efficacy of the electrical stimulation, without the need for any messy gels.

As should be appreciated from the foregoing the subject braces are quite effective for applying electrical stimulation, e.g., HVPC, while retaining heat within the portion of the wearer's body to which the electrical stimulation is applied. Thus, the braces of this invention combine compression and heat with all of the benefits of electrical stimulation. In particular, the subject braces, when used, should increase local circulation, relax muscles spasms, prevent retardation of disuse atrophy and maintain or increases range of motion. The wide coverage of the electrically conductive mesh ensures that full recruitment of a large muscle can be achieved with the subject invention.

The subject braces can be used to apply treatment under various conditions of service. In particular, the braces allow treatment to be given during an athletic event or other strenuous activity, which heretofore had been difficult, if not impossible to perform. In this regard the subject braces allow the wearer to participate in an athletic event using the brace without it being electrically connected to the electrical stimulation system, and then receive treatment on the sidelines during a rest period. In particular, when electrical stimulation treatment is desired all that is necessary is to snap the connectors of the electrical stimulation system to the connectors of the brace. If the electrical stimulation unit is sufficiently small and portable, and if the athletic event permits it, the electrical stimulation system may be connected to the brace to apply electrical stimulation to the affected body part during the athletic event (and thus not limited to use on the sidelines or in a training room.

Moreover, the use of -the neoprene sleeve over the electrically conductive fabric, results in a brace that is quite rugged and long-lasting. Thus, the braces of this invention are not only particularly suitable for active use, but also long-term use, e.g., treatment of chronic injuries or conditions.

Since the construction of each of the subject braces is rather simple, each brace can be readily fabricated from one or more sheet of fabric-covered-neoprene or some other elastomeric material, with the electrically conductive fabric secured to the inner surface thereof at any desired position. Moreover, each brace can be shaped/constructed for use on any type of joint, on any limb, or on any other portion of a person's body which would benefit from the application of electrical stimulation, heat retention, compression and/or support. Thus, as mentioned earlier, it is contemplated that any brace constructed in accordance with this invention could make use of either a preformed sleeve or a wrap-around sheet. Both types of construction enable the brace to be readily applied. However, the former arrangement more fully allows the user to adjust or customize the brace to his/her particular anatomy, while balancing compression and comfort via the releasable securement means, e.g., the hook and loop closures. The externally located terminal connectors, e.g., the snaps, allow for quick and easy application of HVPC while the brace is in place. The soft cloth mesh forming the electrical terminal provides comfortable stimulation across its entire surface, without the need for messy electrically conductive gels, creams, or liquids.

It should be pointed out at this junction that other materials, than those described heretofore, can be used to make the braces of this invention. For example, neoprene having a tufted fabric covering may not be used, i.e., the neoprene may not be covered by any fabric (such as in the case of a preformed-sleeve) or may be covered by a non-tufted fabric, such as smooth nylon. In the case where the brace is of the wrap-around design and the sheet member which is to form the sleeve does not include a plush fabric covering, the outer surface of that sheet should include at least patches of a plush or multi-loop, e.g., VELCRO®, component fixedly secured thereto for engagement by a cooperating multi-hook, e.g., VELCRO, component of the mounting straps. In fact, other releasably securable means can be used in lieu of VELCRO components, if desired. Moreover, in some cases, it may not be desired to use neoprene as the material of the sleeve member. Thus, other elastic materials, with or without cushioning and thermal retention properties may be used. Further still, the sleeve member can be formed of plural sheets fixedly secured, e.g., sewn, together, or of a unitary sheet, i.e., a single piece of material. Once fabricated and assembled, the brace is quite compact. This enables it to be transported and warehoused inexpensively.

As should be appreciated by those skilled in the art the subject brace is quite effective for applying electrical stimulation, while retaining heat within the portion of the wearer's body to which the electrical stimulation is applied. Moreover, the construction of the brace renders it suitable to be readily applied and adjusted to provide customized support. Further still, its construction is very simple. Thus, it can be readily fabricated from a sheet of fabric-covered-neoprene or some other elastomeric material with the electrically conductive fabric secured to the inner surface thereof at any desired position. Once fabricated and assembled, its generally compact shape enables it to be transported and warehoused inexpensively.

Without further elaboration, the foregoing will so fully illustrate our invention that others may, by applying current or future knowledge, readily adapt the same for use under the various conditions of service.

We claim:

1. A brace for disposition on a portion of a person to provide mechanical support, heat retention, and electrical stimulation thereto, said brace comprising:

(a) sleeve means formed of an electrically and thermally insulative elastomeric material arranged to be wrapped about and stretched to be releasably secured to the portion of the person's body to conform thereto, said sleeve means having an inner surface, portions of which engage the skin of the person when said sleeve means is in place thereon, said sleeve means having an opening therein, said sleeve means being operative to retain heat in the portion of the person's body about which said sleeve means is disposed and to provide mechanical support therefor, (b) electrically conductive terminal means comprising a unitary, stretchable, flexible, electrically conductive fabric secured to at least a major portion of said inner surface of said sleeve means and stretchable therewith for direct engagement with the skin of the person when said sleeve means is in place, and (c) quick operating electrical connector means comprising an electrically conductive member fixedly secured to said conductive terminal means in electrical continuity therewith and including a portion extending through said opening in said sleeve means, said extending portion of said electrical conductive member being arranged to be quickly releasably secured to a mating electrically conductive member coupled to a source of electrical energy so that electrical stimulation is provided by the engagement of said electrically conductive terminal means to the skin of the person.

2. The brace of claim 1 wherein said elastomeric material comprises neoprene.

3. The brace of claim 1 wherein said sleeve means comprises a preformed sleeve.

4. The brace of claim 3 wherein said elastomeric material comprises neoprene.

5. The brace of claim 1 wherein said sleeve means comprises a sheet of said electrically and thermally insulative elastomeric material arranged to be wrapped into the form of a sleeve, and wherein said brace additionally comprises releasably securable mounting means for releasably mounting said sleeve on the portion of the person.

6. The brace of claim 5 wherein said releasably securable mounting means comprises at least one mounting strap fixedly secured to a portion of said sleeve means.

7. The brace of claim 6 wherein said sleeve includes hook and loop fastening means for releasably securing said mounting strap to a portion of said sleeve.

8. The brace of claim 1 wherein said electrically conductive member comprises a snap.

* * * * *